US009012962B2

(12) United States Patent
Henneck et al.

(10) Patent No.: US 9,012,962 B2
(45) Date of Patent: Apr. 21, 2015

(54) GAS SENSOR AND FLIP-CHIP METHOD FOR ITS MANUFACTURE

(75) Inventors: Stefan Henneck, Leonberg (DE); Ralf Schmidt, Gerlingen (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 13/002,188

(22) PCT Filed: May 4, 2009

(86) PCT No.: PCT/EP2009/055343
§ 371 (c)(1),
(2), (4) Date: Dec. 30, 2010

(87) PCT Pub. No.: WO2010/000518
PCT Pub. Date: Jan. 7, 2010

(65) Prior Publication Data
US 2011/0147803 A1 Jun. 23, 2011

(30) Foreign Application Priority Data

Jul. 4, 2008 (DE) .......................... 10 2008 040 187

(51) Int. Cl.
G01N 27/403 (2006.01)
G01N 27/414 (2006.01)
(52) U.S. Cl.
CPC .................................. G01N 27/4141 (2013.01)
(58) Field of Classification Search
USPC .............................................. 257/3, 253, 433
See application file for complete search history.

(56) References Cited

U.S. PATENT DOCUMENTS

| 5,505,837 A * | 4/1996 | Friese et al. .................. 204/425 |
| 6,351,390 B1 * | 2/2002 | Mayer et al. .................. 361/760 |
| 8,124,953 B2 * | 2/2012 | Elian et al. ........................ 257/3 |

(Continued)

FOREIGN PATENT DOCUMENTS

| DE | 198 14 857 | 10/1999 |
| DE | 199 56 744 | 6/2001 |

(Continued)

OTHER PUBLICATIONS

Fleischer M et al "Low-power gas sensors based on work-function measurement in low-cost hybrid flip-chip technology" Sensors and Actuators B (Chemical) Elsevier, Switzerland, vol. BS0, No. 3, l Dec. 2001, pp. 169-173, XP004311804, ISSN :0925-4005.*

(Continued)

*Primary Examiner* — Thao X Le
*Assistant Examiner* — Laura Dykes
(74) *Attorney, Agent, or Firm* — Kenyon & Kenyon LLP

(57) ABSTRACT

A sensor element is described that includes at least one semiconductor component having a gas-sensitive layer which is attached to a substrate by the flip-chip method, the gas-sensitive layer facing the substrate and a supply arrangement being provided to supply a gas to be examined to the gas-sensitive layer. The semiconductor component is enclosed in a casing. Also described is a method for manufacturing the sensor element, in which a semiconductor component having a gas-sensitive layer is attached by the flip-chip method to a substrate in such a way that the gas-sensitive layer faces the substrate. After that, the casing is applied by a plasma sputtering method, in particular an atmospheric plasma sputtering method. Finally, a use of the sensor element in the exhaust system of an internal combustion engine is also described.

31 Claims, 2 Drawing Sheets

(56) References Cited

U.S. PATENT DOCUMENTS

| | | | |
|---|---|---|---|
| 2005/0097941 A1* | 5/2005 | Sandvik et al. | 73/31.06 |
| 2007/0220954 A1* | 9/2007 | Fleischer et al. | 73/31.05 |
| 2008/0250847 A1* | 10/2008 | Kitani et al. | 73/31.05 |
| 2009/0159447 A1* | 6/2009 | Cui et al. | 204/431 |

FOREIGN PATENT DOCUMENTS

| | | |
|---|---|---|
| DE | 10 2004 019 640 | 11/2005 |
| DE | 10 2005 008 051 | 8/2006 |
| EP | 1 003 035 | 5/2000 |
| EP | 1 707 952 | 10/2006 |
| JP | 3-172749 | 7/1991 |
| JP | 2005-217082 | 8/2005 |
| JP | 2005-241576 | 9/2005 |
| JP | 2008-70200 | 3/2008 |
| WO | 98/27411 | 6/1998 |
| WO | WO 2005083149 A1 * | 9/2005 |

OTHER PUBLICATIONS

Fleischer M et al : "Low-power gas sensors based on work-function measurement in low-cost hybrid flip-chip technology" Sensors and Actuators B (Chemical) Elsevier, Switzerland, vol. B80, No. 3, Dec. 1, 2001, pp. 169-173, XP004311804, ISSN : 0925-4005.

* cited by examiner

GAS SENSOR AND FLIP-CHIP METHOD FOR ITS MANUFACTURE

This application claims priority to German Patent Application No. 10-2008-040187.0, filed on Jul. 4, 2008, the disclosure of which is hereby incorporated by reference herein in its entirety.

FIELD OF THE INVENTION

The present invention is directed to a sensor element, having at least one semiconductor component with a gas-sensitive layer. Further, the present invention relates to a method for manufacturing such a sensor element and the use thereof.

BACKGROUND INFORMATION

Sensor elements that have at least one semiconductor component with a gas-sensitive layer are generally used to detect components of a gas mixture. Semiconductor components having a gas-sensitive layer are generally gas-sensitive field-effect transistors. In such gas-sensitive field-effect transistors the gate electrode has a coating applied to it, to which gas molecules may adsorb and thereby by way of the charge carrier density modify the characteristic curve of the transistor. That is an indication of the presence of the gas in question. The material used for the coating is one that is selective for certain particular gases that it is desired to detect. For that purpose, the coating generally, speaking contains a catalytically active material. By using different gas-sensitive field-effect transistors, each having a specific coating on the gate electrode, different gases may be detected.

Sensor elements for detecting components of gases may, for example, also be used in motor vehicle exhaust systems. Using such sensor elements, the presence of, for example, nitrogen oxides, ammonia, or hydrocarbons in the exhaust gas may be detected. However, the high temperatures of the exhaust gas from an internal combustion engine subject the sensor elements to severe stresses. In addition, particles may be contained in the exhaust gas that might abrade the coating off the gate electrode. This means that protection has to be provided for the coating on the gate electrode, but at the same time its functionality must not be impaired by such protection.

A gas-sensitive field-effect transistor having a sensitive layer having open pores is discussed, for example, in DE-A 10 2005 008 051.

SUMMARY OF THE INVENTION

A sensor element formed according to the present invention has at least one semiconductor component with a gas-sensitive layer, which is attached to a substrate by the flip-chip method, the gas-sensitive layer facing the substrate, and an arrangement for, supplying a gas to be examined to the gas-sensitive layer being provided. The semiconductor component is enclosed in a casing.

Attachment of the semiconductor component using the flip-chip method and its subsequent enclosure in a casing protect the semiconductor component against external influences. Thus not only is the gas-sensitive layer already protected by its facing toward the substrate and not away from it toward the environment but additionally, the casing also ensures that no harmful components in the surrounding medium may interact with the semiconductor component. In this way it is possible effectively to prevent any damage of the semiconductor component.

The arrangement for supplying the gas to be examined to the gas-sensitive layer include a porous layer, situated between the semiconductor component and the substrate, one area of the porous layer not being covered by the casing. The gas to be examined may penetrate into the porous layer through the area of it that is not covered by the casing. The gas to be examined is routed through the porous layer to the gas-sensitive layer. The use of a porous layer prevents non-gaseous components of the gas to be examined, for example particles contained in it, from reaching the gas-sensitive layer. In this way the porous layer acts as an additional protective layer for the gas-sensitive layer.

The porous layer may include a ceramic material having open pores. Ceramic materials having open pores for inclusion in the porous layer that may be used are aluminum oxide, zirconium oxide, cordierite and mixtures thereof.

The porous layer may be applied to the substrate before the attachment of the semiconductor component. At the positions where the substrate is bonded with the semiconductor component, recesses are made in the porous layer. As an alternative it is also possible, for example, to incorporate feedthroughs into the porous layer. For example, the porous layer is applied by a serigraphic process, generally followed by a sintering phase. The porous layer may, however, for example, also be applied by a plasma sputtering method, or by doctor blade, from a dispenser, or by tampon printing. It may be preferable, however, for the porous layer to be applied by a serigraphic process, in the course of which the porosity of the porous layer may be set through the use, for example, of pore-formers. In addition, a serigraphic process makes possible a precise orientation of the porous layer. The serigraphic process makes it simple to achieve a planar surface.

In an alternative specific embodiment, a duct for the gas supply is formed in the substrate, extending from the gas-sensitive layer of the semiconductor component at one end to a position outside the casing at the other. The gas-supply duct may, for example, be milled into the substrate, the inlet being positioned on the same side of the substrate as the semiconductor component. It may be preferable if the duct is covered and only a small inlet opening left uncovered, so that no components of the gas to be examined that could damage the gas-sensitive layer may enter the duct.

However, it may be preferable for the duct to be in the form of a passage in the substrate. In this form, there is an access opening on the underside of the substrate and the semiconductor component is located directly, above the duct on the top of the substrate.

In order to prevent particles contained in the gas flow, in particular, from reaching the gas-sensitive layer, it may be preferable for the duct to be filled with a porous material. The porous material with which the duct is filled is advantageously the same as that used for the porous layer described above. The porous material is introduced into the duct using the same methods as are used for application of the porous layer. In addition to the duct, it is moreover possible for a porous layer, as described above, to be formed between the substrate and the semiconductor component. If a substrate is provided, then the porous layer, however, is completely covered by the casing, since the gas is supplied through the duct.

In order that the gas to be examined, which under certain circumstances might contain components that could harm the semiconductor component, comes into contact only with the gas-sensitive layer, it is possible, when a porous layer is placed between the semiconductor component and the substrate or a duct in the substrate, through which the gas is supplied to the gas-sensitive layer, to make the casing gastight. With a gas-tight casing, gaseous components, in particular, of the gas to be examined, are also kept away from the semiconductor component.

As an alternative to a gas-tight casing and as an example, a porous layer, through which the gas is supplied to the gas-sensitive layer or to a duct in the substrate, it is also possible to make the casing porous and to install the semiconductor component and the substrate at some distance from one another, so that the gas to be examined is supplied to the gas-sensitive layer through the porous casing and between the semiconductor component and the substrate. In this specific embodiment it must be ensured that, when the semiconductor component is installed on the substrate, a requisite clearance is maintained between the semiconductor component and the substrate, in order to allow the gas to be examined to reach the gas-sensitive layer.

As an alternative, it is also possible for the casing to be porous and for a duct to be formed below the semiconductor component in the substrate, so that the gas to be examined is supplied to the gas-sensitive layer through the porous casing and through the duct. In this specific embodiment it is also possible to place the semiconductor component directly on the substrate, without leaving a gap between the semiconductor component and the substrate.

Instead of a gap between the semiconductor component and the substrate, it is also possible, as an alternative, to have a porous layer between the semiconductor component and the substrate. Also, the duct may be filled with a porous layer. If a porous layer is included between the semiconductor component and the substrate, then the requisite clearance between the semiconductor component and the substrate is set by the porous layer.

The casing in which the semiconductor component is enclosed may include at least one material from the group consisting of aluminum oxide, zirconium oxide, cordierite and glasses. It may be preferable, however, if the casing is made from aluminum oxide, zirconium oxide, cordierite or mixtures of those materials.

The method for manufacturing the sensor elements may include the following steps:
  (a) attaching a semiconductor component having a gas-sensitive layer by using a flip-chip method to a substrate in such a way that the gas-sensitive layer faces the substrate and a gas to be examined may be supplied to the gas-sensitive layer;
  (b) applying the casing after the semiconductor component is attached.

It may be preferable if the casing is applied using a plasma sputtering method, in particular an atmospheric plasma sputtering method. By applying the casing using the plasma sputtering method, precise adjustment of the porosity of the casing is possible. Thus the casing may be made either very porous, less porous or completely gas impermeable. Attachment of the semiconductor component by using the flip-chip method, with the gas-sensitive layer facing the substrate, provides an additional protection for the gas-sensitive layer during application of the casing, such that the sensitive structures of the gas-sensitive layer cannot be damaged by the plasma sputtering. In addition, the plasma sputtering method makes it possible to build up the casing in a specific desired manner. Gradients, for example in the porosity of the casing, may also be implemented.

One particular advantage of atmospheric plasma sputtering is that generally speaking no subsequent heat treatment is required. In addition, the application may be performed at moderate temperatures, in other words in the range between 20° C. and 300° C. Furthermore, the coefficient of thermal expansion of the casing may be adapted, for example through the porosity or the mixture ratio of the ceramic materials used for the casing, and thermally induced stresses may be avoided.

The use of an atmospheric plasma sputtering method has the further advantage that the chamber in which the casing is applied does not need to be evacuated. That permits faster throughput, thereby reducing costs.

As an alternative to the application of the casing by, plasma sputtering it is also possible to make use of any other coating process known to those skilled in the art. Thus, the casing may in particular be applied using materials that do not need to be sintered at high temperatures, or, in the case of temperature-stable semiconductor components, for example also from a dispenser or by tampon printing.

The semiconductor component having the gas-sensitive layer is, for example, a chemosensitive field-effect transistor. In the case of a chemosensitive field-effect transistor, the gas-sensitive layer is generally speaking the gate electrode. For example, a chemical reaction of the gas to be detected occurs at the gas-sensitive layer, whereby the characteristic of the gas-sensitive layer, for example its electrical conductivity, changes. For this purpose, the gas-sensitive layer is made, for example, from a porous semiconductor material having a coating that is catalytically active for the gas to be detected.

A sensor element according to the preset invention may be used, for example, to determine the amounts of nitrogen oxides, ammonia, and/or hydrocarbons in the exhaust system of an internal combustion engine, in particular of an internal combustion engine in a motor vehicle. To determine the amounts of nitrogen oxides, ammonia, and/or hydrocarbons different catalytically active substances are used for the gas-sensitive layer, for example, so that the gas-sensitive layer reacts selectively to one of those gases.

Because the semiconductor component is enclosed in a casing, the semiconductor component is protected, for example, from particles present in the exhaust gas, such as soot particles, that may have an abrasive effect. In addition the casing protects the semiconductor component against high temperatures.

Exemplary embodiments of the present invention are shown in the drawings and described in greater detail in the following description.

DETAILED DESCRIPTION

Figure 1:
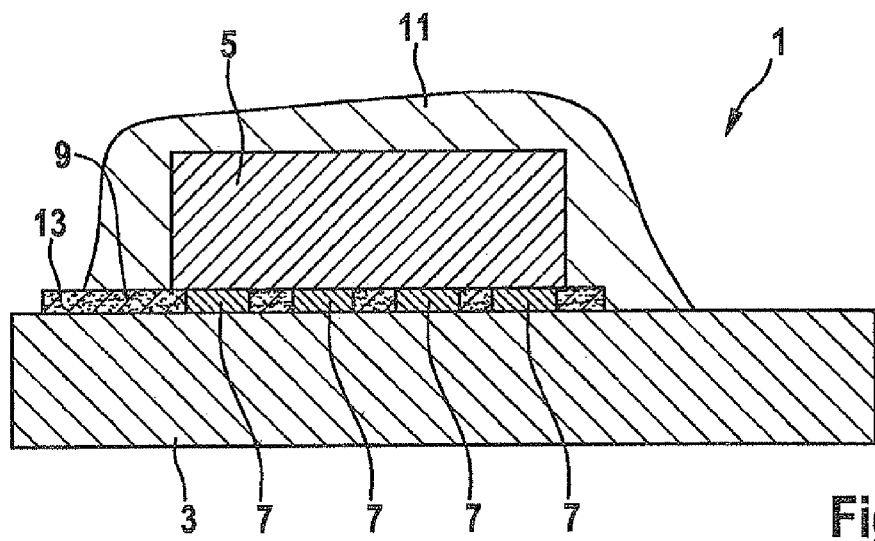
FIG. 1 shows a schematic cross-sectional representation of a sensor element formed according to the present invention in a first specific embodiment.

FIG. 1 shows a cross-sectional representation of a sensor element formed according to the present invention in a first specific embodiment.

Sensor element 1 includes substrate 3, upon which semiconductor component 5 is placed.

Substrate 3 may, for example, include a semiconductor material, for example a semiconductor chip, and may in addition include electrical leads, contact pads, or the like. As an alternative, substrate 3 may, however, also be a printed circuit board, for example, with appropriate tracks applied to it. If substrate 3 is a printed circuit board, then any material known to those skilled in the art from which printed circuit boards are typically manufactured is suitable as the material for the substrate.

Semiconductor component 5 is attached to substrate 3 by a flip-chip method. Using the flip-chip method, the semiconductor component is mounted with its active side facing substrate 3. In this process, semiconductor component 5 is attached, for example, using contact points 7, so-called contact bumps, on substrate 3. Semiconductor component 5 has a gas-sensitive layer, with which, for example, the presence of certain gases in the environment may be detected. A suitable semiconductor component 5, for example, is a gas-sensitive field-effect transistor.

Generally speaking the gas-sensitive layer of semiconductor component 5 is constructed in such a way that that it reacts sensitively to only one specified gas. Detecting, for example, different gases contained in the environment requires several semiconductor components 5. Semiconductor components 5 are then, for example, arranged as an array, on a substrate 3. As an alternative, however, it is also possible to provide an independent sensor element 1 for each component to be detected, with one semiconductor component 5 for each component being positioned on a substrate 3.

As a result of the attachment of semiconductor component 5 on substrate 3 using the flip-chip method, the gas-sensitive layer of semiconductor component 5 faces toward substrate 3. In order that the gas to be examined may reach the gas-sensitive layer of semiconductor component 5, it is therefore necessary to provide a arrangement for supplying the gas. In the specific embodiment shown in FIG. 1 the arrangement for supplying the gas include porous layer which is situated between substrate 3 and semiconductor component 5. Porous layer 9 is permeable to the gas to be examined. The thickness of porous layer 9 may be adjusted on the one hand by, for example, a suitable application method. On the other hand it is also possible, however, for the thickness of porous layer 9 to be set by the clearance between semiconductor component 5 and substrate 3. This clearance results, for example, from the height of contact points 7.

Porous layer 9 may be applied by any suitable method known to those skilled in the art. Porous layer 9 may be applied by a serigraphic process, before the semiconductor component is positioned. The porosity of the layer may then be set, for example, with the aid of a pore-former. If porous layer 9 is applied by serigraphy, porous layer 9 is generally sintered. The material used for porous layer 9 may be one of several ceramic materials, for example aluminum oxide, zirconium oxide, cordierite or mixtures thereof.

According to the present invention semiconductor component 5 is enclosed in casing 11. Casing 11 may be porous or gas-tight. If casing 11 is gas-tight, porous layer 9 is not completely enclosed by casing 11, but an area of porous layer 9 protrudes out of casing 11 between casing 11 and substrate 3. The area of porous layer 9 protruding out of casing 11 is identified by reference numeral 13. Gas penetrates into porous layer 9 via area 13 of porous layer 9 protruding out of casing 11 and is supplied to the gas-sensitive layer of semiconductor component 5.

If casing 11 is porous, so that the gas to be examined may diffuse through casing 11, it is not necessary for porous layer 9 to have an area 13 protruding out of casing 11. In this case, for example, porous layer 9 may be eliminated. In such a case a clearance is created between semiconductor component 5 and substrate 3. The clearance is determined by the height of contact points 7.

Using a porous casing 11, it is, however, also possible for an area 3 of porous layer 9 to protrude out of casing 11.

Casing 11 provides mechanical protection to semiconductor component 5. Protection is established against, for example, abrasive particles that might be contained in a gas being supplied to sensor element 1. In addition, casing 11 also offers protection against any thermal shock stress which might result from the impact of small water droplets contained in the gas flow on heated semiconductor component 5.

Casing 11 may be applied by a plasma sputtering method. The plasma sputtering method makes it possible to set a specified thickness for casing 11. In addition, the porosity of casing 11 may also be set as desired. Thus it is possible, for example, to make casing 11 porous or alternatively gas-tight.

The material for casing 11 may be aluminum oxide, zirconium oxide, cordierite, a glass, or a mixture thereof.

If casing 11 is made porous and a porous layer 9 is provided, casing 11 and porous layer 9 may be made either from the same or from different materials. It may be preferable, however, if casing 11 and porous layer 9 are made from the same material. In addition to the options for the material, it is furthermore also possible for casing 11 and porous layer 9 to be of different porosities. Thus, for example, it possible for porous layer 9 to be more porous than casing 11. Alternatively, it is also possible for casing 11 to be more porous than porous layer 9. As an alternative to a different porosity for casing 11 and porous layer 9 it is, however, also possible for casing 11 and porous layer 9 to have the same porosity.

Because semiconductor component 5 is mounted using a flip-chip method, the gas-sensitive layer of semiconductor component 5 is protected when casing 11 is applied, since the material of casing 11 cannot reach the gas-sensitive layer. This prevents destruction of the potentially sensitive gate structures of a gas-sensitive field-effect transistor.

Figure 2:
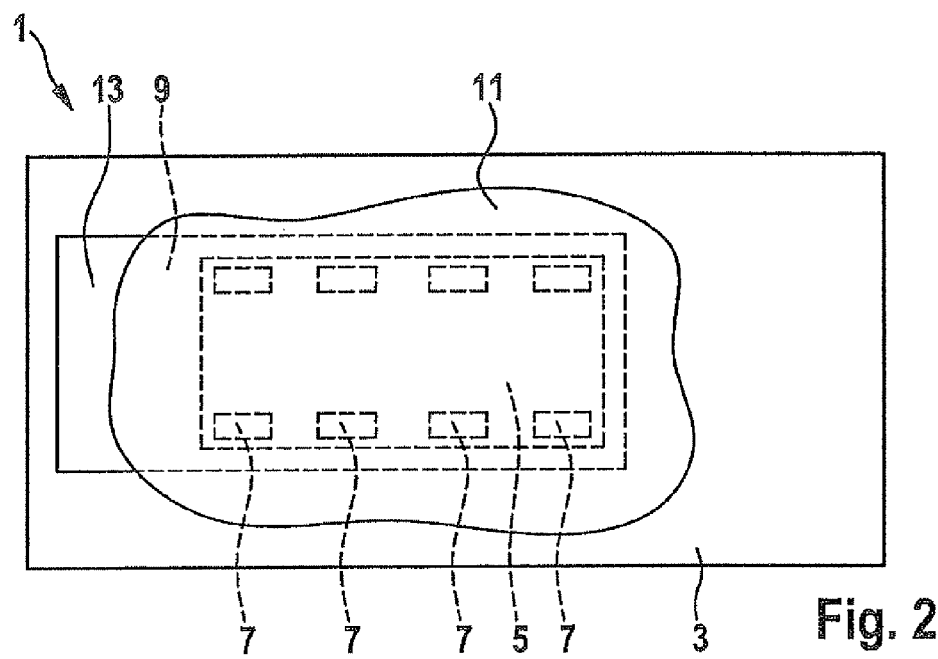
FIG. 2 shows a top view of a sensor element according to FIG. 1.

FIG. 2 shows a top view of a sensor element according to FIG. 1.

As is apparent from the representation according to FIG. 2, porous layer 9 protrudes on all sides out of semiconductor component 5. Porous layer 9 thereby acts as protection for the bottom of semiconductor component 5. Since porous layer 9 is larger than semiconductor component 5, no area of the bottom of semiconductor component 5 is exposed.

In the specific embodiment shown here porous layer 9 protrudes on one side below casing 11. However, area 13 of porous layer 9 protruding out of casing 11 may protrude under casing 11 on all sides. In such a case casing 11 is fully in contact with porous layer 9.

Figure 3:
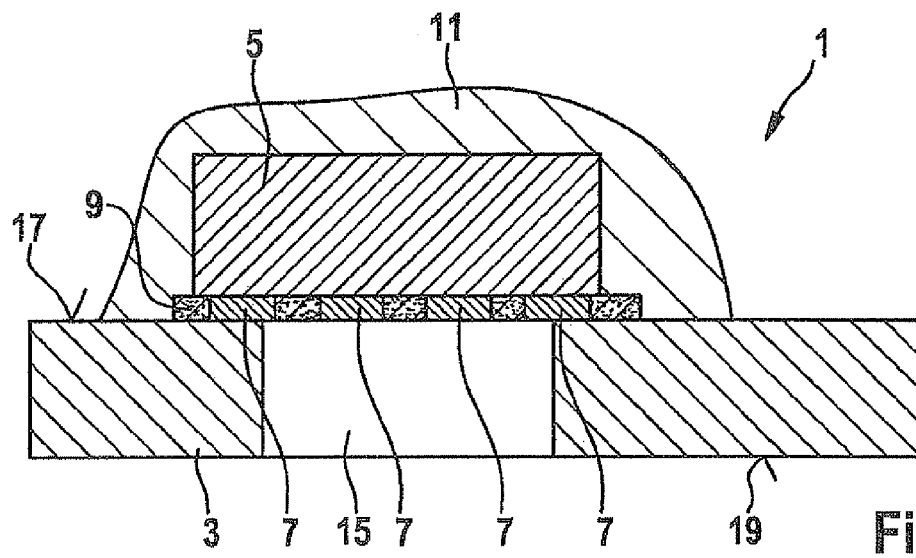
FIG. 3 shows a schematic representation of a sensor element according to the present invention in a second specific embodiment.

A sensor element 1 in an alternative specific embodiment is shown in FIG. 3. The specific embodiment shown in FIG. 3 differs from the specific embodiment shown in FIGS. 1 and 2 in that porous layer 9 is completely enclosed in casing 11. In order to provide access for gas to semiconductor component 5, passage 15 is formed in substrate 3. Passage 15 may extend, as shown in FIG. 3, below semiconductor component 5 from top 17 of substrate 3, on which semiconductor component 5 is attached, to bottom 19 of substrate 3.

Alternatively it is also possible, instead of passage 15, for a duct to be formed in substrate 3, extending along top 17 and protruding out of casing 11. If passage 15 or a duct is formed in substrate 3, through which the gas to be examined may be supplied to the gas-sensitive layer of semiconductor component 5, porous layer 9 may be eliminated. In this case a clearance is formed between substrate 3 and semiconductor component 5. It is also possible when a duct or passage 15 in present in substrate 3 for semiconductor component 5 to be placed directly on substrate 3, without having a clearance between semiconductor component 5 and substrate 3.

Additionally, when a duct or passage 15 is present in substrate 3, casing 11 may be gastight. The gas reaches the gas-sensitive layer of semiconductor component 5 through the duct in substrate 3 or through passage 15.

In order to prevent particles, for example, that might be contained in the gas and under certain circumstances might result in mechanical damage to the gas-sensitive layer of semiconductor component 5, from reaching the gas-sensitive layer, it may be preferable if passage 15 or the duct, if one has been formed in substrate 3, is filled with a porous material, which is gas-permeable but prevents the passage of particles.

If passage 15 or a duct is formed in substrate 3, it must be ensured that no moisture is able to penetrate into it, since moisture may result in damage of semiconductor component 5.

Figure 4:
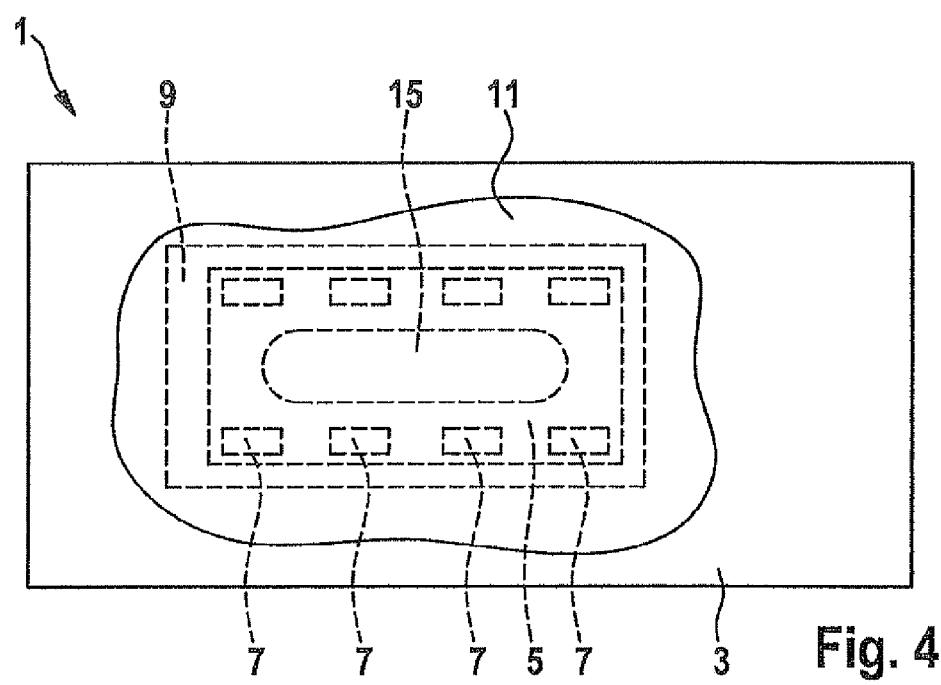
FIG. 4 shows a top view of a sensor element according to FIG. 3.

FIG. 4 shows a top view of sensor element 1 according to FIG. 3. In the specific embodiment shown here it is apparent that passage 15 is formed in the shape of an elongated hole.

With the aid of this shape a greatest possible area of the gas-sensitive layer of semiconductor component 5 is open to the gas. In addition to being formed as an elongated hole, as shown in FIG. 4, passage 15 may have any other shape. It is also possible that instead of only one passage 15, several passages may be provided. These may be executed, for example, in the form of bore holes. Also any other cross-sectional shape is possible for passage 15.

In addition to a gastight casing 11 it is alternatively also possible to apply a casing 11 that is porous and thus gas-permeable. In the case of a porous casing 11, area 13 of porous layer 9 protruding out of casing 11, as shown in FIGS. 1 and 2, may be eliminated. In addition, it is not necessary to provide a passage 15 in substrate 3, if substrate 3 and semiconductor component 5 are at some distance from one another. This may be ensured, for example, with the aid of porous layer 9. Using a porous casing 11 it is also possible, for example, to eliminate porous layer 9. The requisite clearance between semiconductor component 5 and, substrate 3, which is needed for the gas to be supplied to the gas-sensitive layer, is then set with the aid of the height of contact points 7. Additionally, using a porous casing 11 it is possible to locate semiconductor component 5 directly on substrate 3 without a clearance. In this case a duct is formed in substrate 3, which protrudes below semiconductor component 5, so that the gas to be examined is supplied through the porous casing and the duct to the gas-sensitive layer of semiconductor component 5.

What is claimed is:

1. A sensor element, comprising:
   a substrate;
   at least one semiconductor component having a gas-sensitive layer, wherein the gas-sensitive layer faces the substrate; and
   a supply arrangement including a porous layer to supply a gas to be examined to the gas-sensitive layer; wherein:
   the at least one semiconductor component is enclosed in a casing;
   the porous layer is situated between the at least one semiconductor component and the substrate and at least a portion of the porous layer is in contact with the casing, and
   an area of the porous layer protrudes out of the casing and the area contacts an area not protruding out of the casing, the entire area protruding from the casing being exposed to the gas.

2. The sensor element of claim 1, wherein the area of the porous layer protruding out of the casing is not covered by any other components of the sensor element.

3. The sensor element of claim 2, wherein the porous layer contains at least one porous ceramic material having open pores.

4. The sensor element of claim 2, wherein the casing is gastight.

5. The sensor element of claim 1, wherein to supply the gas, a duct is formed in the substrate, opening to the gas-sensitive layer of the at least one semiconductor component at the one end and to a position outside the casing at the other.

6. The sensor element of claim 5, wherein the duct is formed as a passage in the substrate.

7. The sensor element of claim 5, wherein a longitudinal axis of the duct is parallel to a longitudinal axis of the substrate.

8. The sensor element of claim 1, wherein the casing is porous and the at least one semiconductor component and the substrate are situated at a specified distance from one another, so that the gas to be examined is supplied to the gas-sensitive layer through the porous casing and the clearance between the at least one semiconductor component and the substrate.

9. The sensor element of claim 1, wherein the casing is porous and a duct is formed in the substrate below the at least one semiconductor component, so that the gas to be examined is supplied to the gas-sensitive layer through the porous casing and through the duct.

10. The sensor element of claim 1, wherein the casing contains at least one material from at least one of an aluminum oxide, a zirconium oxide, a cordierite and a glass.

11. The sensor element of claim 1, wherein the at least one semiconductor component with the gas-sensitive layer is a chemosensitive field-effect transistor.

12. The sensor element of claim 1, wherein the sensor element determines the amount of at least one of nitrogen oxides, ammonia and hydrocarbons in an exhaust system of an internal combustion engine in a motor vehicle.

13. The sensor element of claim 1, wherein the area of the porous layer protruding out of the casing is not covered by any other components of the sensor element, wherein the porous layer contains at least one porous ceramic material having open pores, wherein a duct is formed in the substrate to supply the gas, opening to the gas-sensitive layer of the at least one semiconductor component at the one end and to a position outside the casing at the other, and wherein the duct is formed as a passage in the substrate, and wherein the casing is gastight.

14. The sensor element of claim 13, wherein the at least one semiconductor component with the gas-sensitive layer is a chemosensitive field-effect transistor.

15. The sensor element of claim 13, wherein the sensor element determines the amount of at least one of nitrogen oxides, ammonia and hydrocarbons in an exhaust system of an internal combustion engine in a motor vehicle.

16. The sensor element of claim 13, wherein a longitudinal axis of the duct is parallel to a longitudinal axis of the substrate.

17. The sensor element of claim 1, wherein the casing is porous and the at least one semiconductor component and the substrate are situated at a specified distance from one another, so that the gas to be examined is supplied to the gas-sensitive layer through the porous casing and the clearance between the at least one semiconductor component and the substrate.

18. The sensor element of claim 17, wherein the casing contains at least one material from at least one of an aluminum oxide, a zirconium oxide, a cordierite and a glass.

19. The sensor element of claim 1, wherein the casing is porous and a duct is formed in the substrate below the at least one semiconductor component, so that the gas to be examined is supplied to the gas-sensitive layer through the porous casing and through the duct.

20. The sensor element of claim 19, wherein the casing contains at least one material from at least one of an aluminum oxide, a zirconium oxide, a cordierite and a glass.

21. A method for manufacturing a sensor element, the method comprising:
  (a) attaching a semiconductor component having a gas-sensitive layer using a flip-chip method to a substrate so that the gas-sensitive layer faces the substrate and a gas to be examined may be supplied to the gas-sensitive layer;
  (b) applying a porous layer; and
  (c) applying a casing over the porous layer such that the casing is in contact with at least a portion of the porous layer, and an area of the porous layer protrudes out of the casing after the semiconductor component is attached and the entire area protruding from the casing is exposed to the gas;
  wherein the sensor element, includes: the substrate, the semiconductor component having the gas-sensitive layer;
  wherein the gas-sensitive layer faces the substrate;
  wherein a supply arrangement includes the porous layer supplying the gas to be examined to the gas-sensitive layer;
  wherein the semiconductor component is enclosed in the casing.

22. The method of claim 21, wherein the casing is applied through an atmospheric plasma sputtering method.

23. The method of claim 21, wherein the area of the porous layer protruding out of the casing is not covered by any other components of the sensor element, wherein the porous layer contains at least one porous ceramic material having open pores, wherein a duct is formed in the substrate to supply the gas, opening to the gas-sensitive layer of the at least one semiconductor component at the one end and to a position outside the casing at the other, and wherein the duct is formed as a passage in the substrate, and wherein the casing is gastight.

24. The method of claim 23, wherein the at least one semiconductor component with the gas-sensitive layer is a chemosensitive field-effect transistor.

25. The method of claim 23, wherein the sensor element determines the amount of at least one of nitrogen oxides, ammonia and hydrocarbons in an exhaust system of an internal combustion engine in a motor vehicle.

26. The method of claim 23, wherein a longitudinal axis of the duct is parallel to a longitudinal axis of the substrate.

27. The method of claim 23, wherein the casing is applied through an atmospheric plasma sputtering process.

28. The method of claim 21, wherein the casing is porous and the at least one semiconductor component and the substrate are situated at a specified distance from one another, so that the gas to be examined is supplied to the gas-sensitive layer through the porous casing and the clearance between the at least one semiconductor component and the substrate.

29. The method of claim 28, wherein the casing contains at least one material from at least one of an aluminum oxide, a zirconium oxide, a cordierite and a glass.

30. The method of claim 21, wherein the casing is porous and a duct is formed in the substrate below the at least one semiconductor component, so that the gas to be examined is supplied to the gas-sensitive layer through the porous casing and through the duct.

31. The method of claim 30, wherein the casing contains at least one material from at least one of an aluminum oxide, a zirconium oxide, a cordierite and a glass.

* * * * *